(12) United States Patent
Papadimitrakopoulos et al.

(10) Patent No.: US 10,820,845 B2
(45) Date of Patent: Nov. 3, 2020

(54) CONTINUOUS ASSESSMENT OF BIOLOGICAL ANALYTES FOR GENERAL WELLNESS

(71) Applicant: Biorasis, Inc., Storrs, CT (US)

(72) Inventors: Fotios Papadimitrakopoulos, West Hartford, CT (US); Antonio Costa, Hartford, CT (US); Faquir C. Jain, Storrs, CT (US); Michael Kastellorizios, Willington, CT (US)

(73) Assignee: Biorasis, Inc., Storrs, CT (US)

( * ) Notice: Subject to any disclaimer, the term of this patent is extended or adjusted under 35 U.S.C. 154(b) by 0 days.

(21) Appl. No.: 15/695,479

(22) Filed: Sep. 5, 2017

(65) Prior Publication Data

US 2018/0064382 A1    Mar. 8, 2018

Related U.S. Application Data

(60) Provisional application No. 62/383,400, filed on Sep. 3, 2016.

(51) Int. Cl.
| | |
|---|---|
| *H04J 14/02* | (2006.01) |
| *A61B 5/1486* | (2006.01) |
| *G01N 27/327* | (2006.01) |
| *A61B 5/00* | (2006.01) |
| *G06F 19/00* | (2018.01) |
| *A61B 5/145* | (2006.01) |
| *A61B 5/1495* | (2006.01) |
| *A61B 5/15* | (2006.01) |

(52) U.S. Cl.
CPC ........ *A61B 5/14865* (2013.01); *A61B 5/0022* (2013.01); *A61B 5/1495* (2013.01); *A61B 5/14532* (2013.01); *A61B 5/14542* (2013.01); *A61B 5/15003* (2013.01); *A61B 5/150786* (2013.01); *G01N 27/3271* (2013.01); *G06F 19/00* (2013.01); *G06F 19/3418* (2013.01); *A61B 5/7246* (2013.01); *A61B 2560/0219* (2013.01); *A61B 2560/0271* (2013.01)

(58) Field of Classification Search
CPC ....... H04B 10/11; H04B 10/1149; H04J 14/02
See application file for complete search history.

(56) References Cited

U.S. PATENT DOCUMENTS

| | | | | |
|---|---|---|---|---|
| 9,337,924 B2* | 5/2016 | Jain | ................... | H04B 10/1149 |
| 2008/0004904 A1* | 1/2008 | Tran | ................... | A61B 5/0006 |
| | | | | 705/2 |
| 2008/0154101 A1* | 6/2008 | Jain | ................... | A61B 5/0017 |
| | | | | 600/309 |
| 2012/0245444 A1* | 9/2012 | Otis | ................... | A61B 5/1486 |
| | | | | 600/345 |
| 2013/0078624 A1* | 3/2013 | Holmes | ................... | C12Q 1/00 |
| | | | | 435/6.11 |

* cited by examiner

*Primary Examiner* — Dzung Tran
(74) *Attorney, Agent, or Firm* — Steven M. McHugh

(57) ABSTRACT

An analyte monitoring platform consisting of a proximity communicator and an implantable biosensor that includes system architecture for biosensor authentication, identification and methods to use analyte sensors for general wellness. The system architecture also permits multi-analyte sensing. In addition, the system and methods can be used for a single analyte or combination of analytes.

13 Claims, 9 Drawing Sheets

| Analyte | Normal Analyte Range (in Blood) |
|---|---|
| Ammonia | 15-50 units/L |
| Amylase | 53-123 units/L |
| Ascorbic Acid | 0.4-1.5 mg/dL |
| Copper | 70-150 μg/dL |
| Creatinine | 0.6-1.2 mg/dL |
| Glucose | 65-125 mg/dL |
| Cholesterol, total | 3-5.5 mmol/L |
| Magnesium | 1.5-2.0 mg/dL |
| Uric acid | 3.0-7.0 mg/dL |
| Ketones | <0.6 mmol/L |
| Lactate (lactic acid) | Venous: 4.5-19.8 mg/dL<br>Arterial: 4.5-14.4 mg/dL |
| Sodium | 135-145 mmol/L |
| Vitamin A | 30-65 μg/dL |
| Vitamin B12 | 130-700 ng/L |
| Vitamin C | 0.4-1.5 mg/dL |
| Vitamin D | 5-75 ng/mL |

FIG. 3

CONTINUOUS ASSESSMENT OF BIOLOGICAL ANALYTES FOR GENERAL WELLNESS

CROSS REFERENCE TO RELATED APPLICATIONS

This application is related to and claims the benefit of the filing date of U.S. Provisional Patent Application Ser. No. 62/383,400 filed Sep. 3, 2016, the contents of which are incorporated herein by reference in its entirety.

FIELD OF THE INVENTION

The present invention relates generally to implantable biosensors and more specifically to biosensors that have signal identification and authentication capabilities that can also provide "general wellness use" indications to an end-user.

BACKGROUND OF THE INVENTION

Mainstream adoption of "general wellness use" devices is leading to an ever increasing demand for health devices that allow for the self-monitoring of biological activities. General wellness devices can be defined as devices that are intended to sustain and promote a general state of health or for intended uses to help alleviate the risks of certain diseases/conditions that have an accepted relationship between such disease/condition and lifestyle behaviors. Conventional self-monitoring devices are designed to measure activities such as heart rate, steps taken, calories burned, sleep quality, distance traveled, speed, etc. These measurements can be used to improve general wellness, such as in weight management or for fitness training. However, the usefulness of this information is limited due to the overall complexity of the human body.

A biosensing platform is a tool that can be used to continuously monitor biological analytes and provide a more in-depth understanding of human physiology and how it reacts to certain daily activities. As defined, a biosensing platform is a device or set of devices that detects any chemical or physical signal change, converts that signal into an electrical or chemical signal and transmits such response to a secondary device (e.g. a watch-like device or proximity communicator). The secondary device can then perform signal processing algorithms and further transmit such information to a computer or cloud-based platform.

Continuous analyte monitoring refers to measuring the amount of one or more particular analytes (e.g. glucose, lactic acid, molecular oxygen, etc.) over a period of time and concomitantly transmitting, storing, and/or displaying such information to the user. The means to continuously measure and monitor analytes can be by non-invasive and/or invasive biosensing platforms. Traditionally, continuous analyte monitoring devices are available for individuals diagnosed with a disease and are not for recreational use. The intended uses of these biosensor platforms are to diagnose and/or manage a particular disease/condition. However, another application is for individuals that do not require diagnosing and/or managing of a disease, but instead for monitoring analytes to gain a comprehensive understanding in personal health (e.g. for recreational use, fitness training, rigorous or non rigorous exercise regiments, weight management regiments, quality of food taken, effect on a variety of stressors (both internal and external), effect on a variety of medication(s) or any other general wellness use.

Both short term and long term analysis of health-related information can lead to a drastic improvement of one's general wellness. Conversely, providing individuals with too detailed information may result in the self-diagnosing of medical diseases or improper use of the device to manage a disease instead of its intended use as general wellness device. Based on this, there must be a proper balance between providing sufficient health information to improve general wellness and restricting health information to prevent the improper use of said devices (i.e. using said devices instead of an approved medical device to manage and/or treat a given disease/condition).

SUMMARY OF THE INVENTION

This invention outlines a system and method for a biosensing platform that provides biological analyte information to users that assists in maintaining a healthy lifestyle, while averting users from using the biosensing platform as a means to diagnose, cure, mitigate, treat, or prevent a specific disease or specific condition. The system, composed of an implantable biosensor and associated proximity communicator (as described in U.S. Pat. No. 9,337,924 B2), further incorporates features to such as (1) a multi-sensing platform, (2) a code detect architecture for optical device identification and authentication, and (3) a non-volatile memory architecture for local data storage of analyte data in the implantable biosensor. The code detect architecture permits device identification, i.e. to optically distinguish between multiple implantable devices. The code detect architecture can also be used with the associated authentication method to ensure that the proximity communicator is uniquely paired with the given implantable device.

The general wellness use method disclosed herein encompasses biosensing platforms that can be used to monitor analytes for purposes such as relating eating habits to general health or how fitness training, rigorous or non rigorous exercise regiments, weight management regiments, quality of food taken, effect on a variety of stressors (both internal and external), effect on a variety of medication (prescribed, over the counter or recreational) or any other general wellness use alter(s) analyte levels. The problem that arises is that users of biosensing platforms may use these devices for medical-related decisions. One example of a medical-related decision is for a person diagnosed with diabetes that measures his/her blood glucose concentration and uses such information to subsequently administer a specific amount of insulin to correct a high blood-glucose level (or hyperglycemia). Such decisions could be life-threatening and should be restricted to devices intended for such use, rather than a general wellness device. The methods outlined in this invention address the aforementioned issue by averting users from making medical-related decisions. Methods outlined herein include providing analyte information (e.g. glucose concentrations) with a substantial time delay (e.g. 1-24 hours), narrowing down the concentration levels of the analyte reported to the user only within "normal" or healthy levels, and/or only providing secondary information such as rates or daily extremum values. As further exemplified, a normal blood glucose concentration range may be from 70-140 mg/dL throughout the day, whereas the blood glucose levels of people diagnosed with diabetes may be both below and above this range (e.g. from 40 to 400 mg/dL and sometimes even beyond these ranges). The working range of the described biosensor platform is limited to only function within the normal range. In this manner, equivalent blood glucose levels outside of this normal blood glucose level range would not be transmitted, recorded, and/or displayed; therefore the user would be required to use an approved medical device (e.g. an FDA-approved medical device) instead for medical-relation decisions

BRIEF DESCRIPTION OF THE DRAWINGS

The foregoing and other features and advantages of the present invention will be more fully understood from the following detailed description of illustrative embodiments, taken in conjunction with the accompanying drawings in which like elements are numbered alike:

FIG. 3 is a table of examples of generalized analyte reference ranges for healthy adults.

DETAILED DESCRIPTION OF THE INVENTION

One purpose of the present invention is to provide a system and method that outlines the transmitting, recording, and/or displaying of analyte levels that enable biosensing platforms to be extended for use by the general population to "general wellness" applications.

Biosensing Platform with Optical Authentication Architecture

In accordance with an embodiment of the present invention, an implantable biosensor platform architecture that enables the reading of one or more analyte sensors with a biosensor authentication process and optical encoding is disclosed herein. The implantable biosensor platform also includes checking the power level of the electrical sources within the implantable biosensor. In addition, the implantable biosensor platform communicates wirelessly between the implantable biosensor and the watch-like device via one or more sets of an optical source (e.g. LED or laser) and a photodetector with matching transmission and detection wavelengths.

Figure 1A:
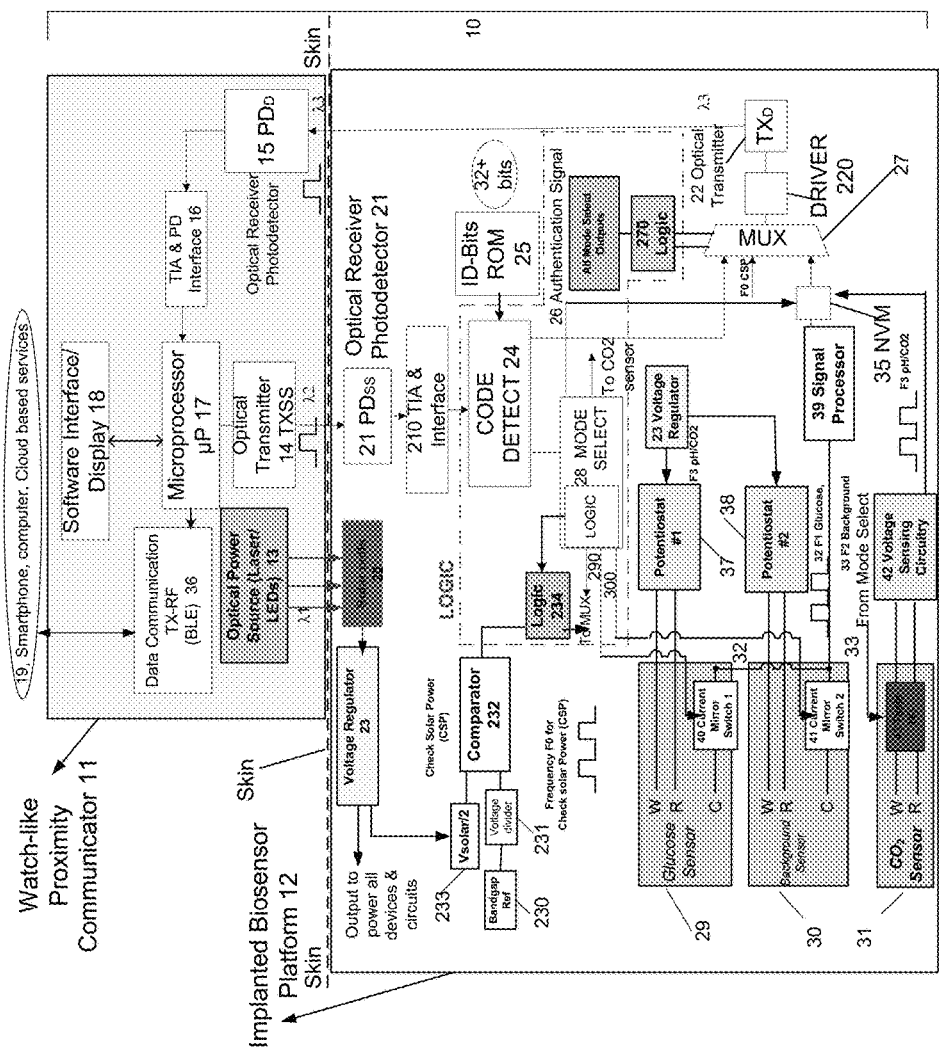
FIG. 1A is a schematic illustrating the architecture of an implantable multi-analyte sensor device with multiple optical transmitters on the proximity communicator and a code detect unit on the implantable biosensor.

Referring to FIG. 1A, the biosensing platform 10 consists of a watch-like proximity communicator 11 and an implanted biosensor 12. The watch-like proximity communicator includes an optical power source 13, an optical transmitter (TXss) 14, an optical receiver/photodetector ($PD_D$) 15, and circuitry 16 such as a trans-impedance amplifier (TIA) and a microprocessor (µP) unit 17. The basic operation of the watch-like proximity communicator 11 is to (1) power the biosensor, (2) transmit information to the biosensor, (3) acquire signals from the biosensor (4) process, store and/or display the data, and (5) transmit either processed or unprocessed data to a smart phone or computer 19 or cloud based service for data storage and/or further processing. Moreover, each data point can be accompanied by metadata such as a timestamp and other physical measurements (e.g. temperature, pressure, hard-bit, etc. readings). The data and metadata can then be transmitted via wireless communication protocols to the computer or cloud-based platform to be displayed to a user or further processed.

The implanted biosensor 12 contains one or more photovoltaic cells (or solar cells) 20 which converts optical power from optical source 13 into electrical power, an optical receiver (PDss) 21, an optical transmitter ($TX_D$) 22, circuitry and sensing elements. The solar cell(s) is powered by the optical power source 13 on the watch-like communicator 11 and is stabilized by a voltage regulator 23. The purpose of the solar cell is to power all the devices and circuitry associated with the implanted biosensor 12. An optical receiver (PDss) 21 is used to communicate with the proximity communicator 11 via optical signals (at wavelength λ2) sent by the transmitter TXss 14. The coded input signal received by PDss 21 is amplified and processed and then analyzed by a code detect processor 24 that provides the implanted biosensor with an authentication signal stored in read only memory (ROM) 25. The authentication signal 26 is used to enable/disable the implanted biosensor from transmitting data. In one embodiment, the authentication signal is to match a code (e.g. 4 to 256-bits) programmed or embedded within the implanted biosensor circuitry. The input signal generated from TXss 14 is fed to mode select unit 28 (mode select circuits are shown in dashed box), to enable one or more analyte sensors (29, 30, 31). It also performs many functions including check solar power (CSP) and check sensor calibration functions.

The architecture has the provision of storing analyte (e.g. glucose) data 32 and background data 33 and CO2 or pH sensor data 34 in the dedicated nonvolatile memory (NVM) 35, which is interfaced with the mode select unit 28. The NVM 35, mode select unit 28 outputs (e.g. F0 check solar power CSP), sensor selection and sensor signals F1 glucose sensor 32, F2 background 33, and F3 other sensors like pH/$CO_2$ 34, lactate, $O_2$, glycerol, etc. not shown) are connected to multiplexing (MUX) circuitry 27. Logic operations 270 are performed to determine the signals that are transmitted. The electrical signal is passed into an optical driving circuit 220 and then to an optical transmitter ($TX_D$) 22. The optical transmitter ($TX_D$) 22 sends information to the proximity communicator 11, which is detected by the optical photodetector ($PD_D$) 15 and associated detection circuitry 16. The sensor data is retrieved at a designated time as programmed by the proximity communicator watch-like device 11. The microprocessor 17 outputs are connected by RF transmitter or Bluetooth (BLE) 36 to smart phone or other devices 19. The glucose sensor 29, glucose background sensor 30 are shown connected to their respective potentiostats 37 and 38, current mirror (not shown) via current mirror switches 40 and 41, and signal processor 39. Other sensors (e.g. CO2) 31, and their accessory circuit 42 are enabled by Tgate switch 43. Implanted biosensor 12 schematic also shows other circuits which are part of voltage regulator 23 and are used to check solar power (CSP) level function. These include bandgap reference 230, voltage divider 231, and voltage regulator output 233 that is compared in a comparator 232 to facilitate logic 234 enabling MUX 27.

Figure 1B:
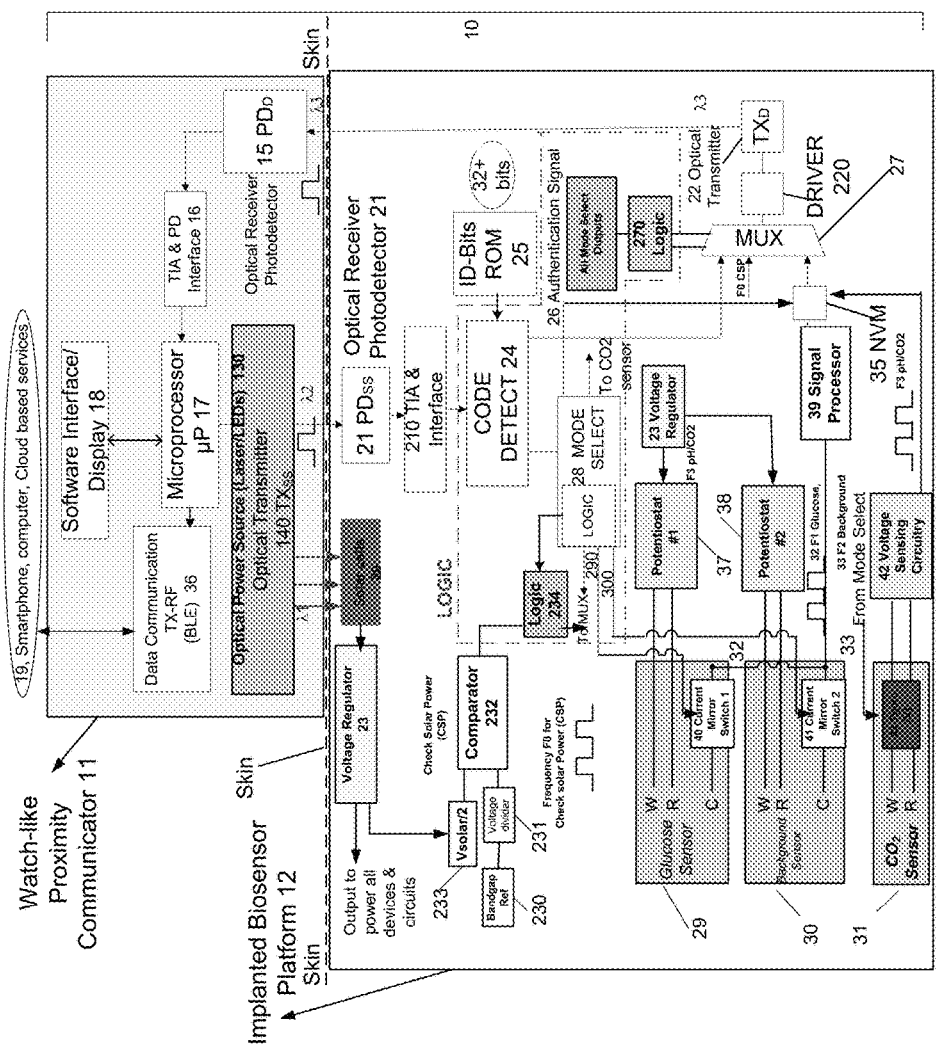
FIG. 1B is a schematic illustrating a second embodiment of FIG. 1A with a single optical source functioning as both a power source and signal transmitter for code detection.

Referring to FIG. 1B, a second embodiment of the platform is outlined wherein the optical power source 130 also acts as the optical transmitter 140. In this manner, the optical power source (wavelength $\lambda 1$) transmits a signal at a frequency that is sufficient to power the solar cell 20 and that is detectable by the optical receiver (PDss) 21 located within the implantable biosensor 12. This frequency signal can then be used in the same manner described above in FIG. 1A (e.g. as an authentication code 26 and for mode select 28). Another variation to this methodology is to eliminate the optical receiver (PDss) 21, and detect directly the optical frequency from the solar cells via a specialized modulation and demodulation circuitry (not shown explicitly).

The architecture further includes features such as solar power check (CSP) and sensor calibration (as disclosed in U.S. Pat. No. 9,337,924 B2). The architecture permits pausing for a small amount of delay (<1 sec) so that the integrity of code detection methods is not compromised in a reasonable time by an unauthorized individual(s) getting hold of the proximity communicator. Integration of an auto-calibration algorithm as well as other control algorithms interfacing with other devices is also envisioned as alternate embodiments.

Method 1—Authentication and Pairing of Biosensing Platform:

The implanted glucose/background sensor architecture includes instructions (using a dedicated optical transmitter TXss 14 (FIG. 1A) or TXss 140 (FIG. 1B) operating at a wavelength of $\lambda_2$) that are transmitted from the proximity communicator 11 and received by the implanted biosensor receiver PDss 21. Once the 32+ bit personalized code stored in the microprocessor (μP) of the proximity communicator 17 and the Identification (ID) programmable or read-only memory (ROM) unit 25 of implanted biosensor is matched (key verification), then the implanted biosensor 12 sends an authentication code 26 by the mode select unit 28 and its associated logic 270. This authentication code is typically composed of a specified frequency of optical pulses or a specified sequence of optical pulse packets with defined frequencies transmitted by optical transmitter $TX_D$ 22 using wavelength $\lambda 3$. Once the authentication code is received by the proximity communicator 11, its microprocessor (μP) 17 instructs it to continue with various sensing and calibration functions.

Figure 2A:
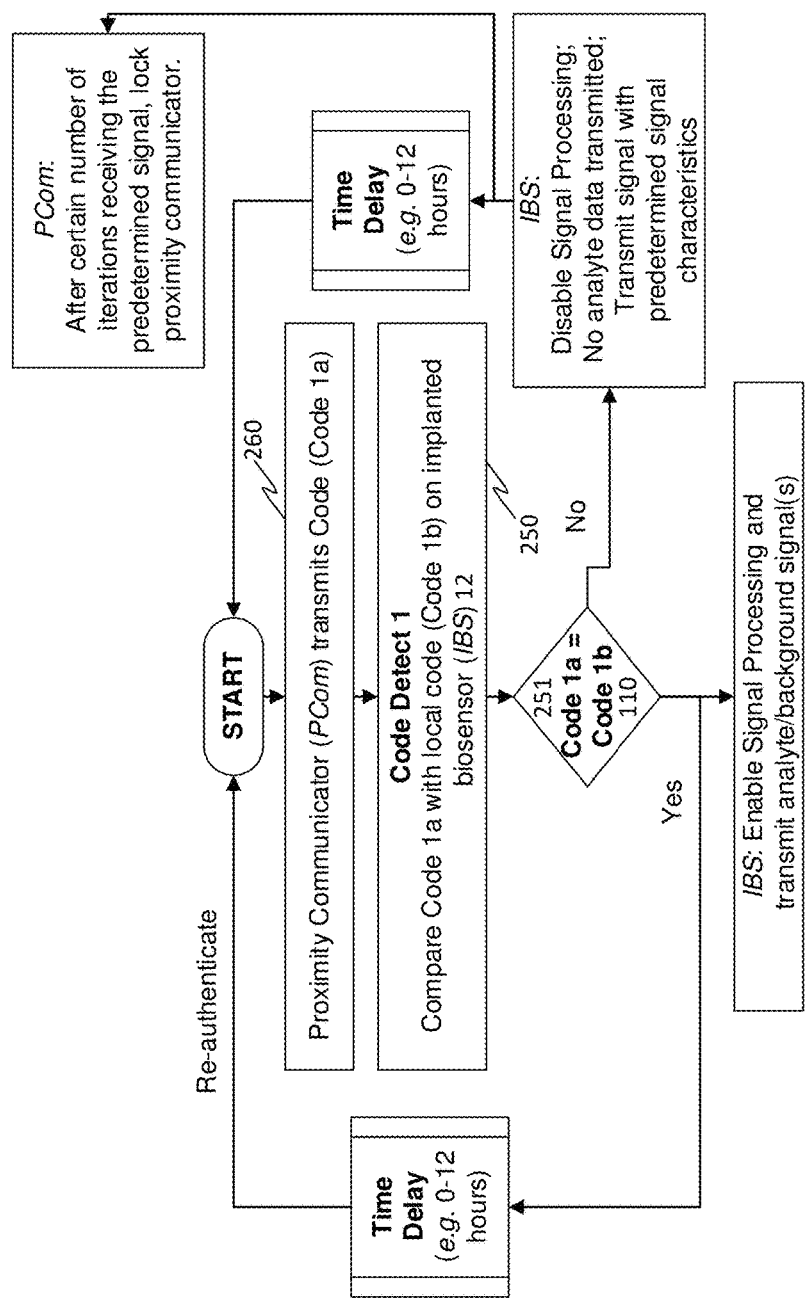
FIG. 2A is a flow diagram illustrating the code detect architecture with a single code that is associated with the proximity communicator and implantable biosensor.

A method for the authentication between the implanted biosensor 12 and the watch-like, proximity communicator 11 is outlined in FIG. 2A. During initialization, the implanted biosensor 12 is powered on by the proximity communicator 11 and the nonvolatile memory (NVM) 35 of the implanted biosensor is disabled. One embodiment of the method for biosensing platform authentication process starts with the proximity communicator 11 transmitting an authentication code 260 (e.g. a 4 to 256-bit code) to the implanted biosensor 12. The implanted biosensor compares the received authentication code with a pre-programmed or hardwired logic authentication code 250. When the received authentication code 260 does not match with the local code 250 (stored in ROM 25) associated with the implanted biosensor 12, the data stored in the NVM 35 is not transmitted. When the received authentication code 260 matches with the local code 250 associated with the implanted biosensor 12, the implanted biosensor transmits a second authentication code 251 to the proximity communicator 11. This second authentication code 251 is compared to a local code 110 on the proximity communicator 11. When the second authentication code does not match the local code 110, the proximity communicator stops transmitting and stops the data acquisition processes. When the local code matches, the nonvolatile memory (NVM) 35 of the implanted biosensor 12 is enabled and the analyte data and background data are transmitted to the proximity communicator 11. Once authenticated, the implanted biosensor 12 continuously transmits analyte data to the proximity communicator 11. Re-authentication will be initiated after a preset time delay (e.g. 0-12 hours). For each case, the process continuously loops as long as the implanted biosensor 12 is powered.

Figure 2B:
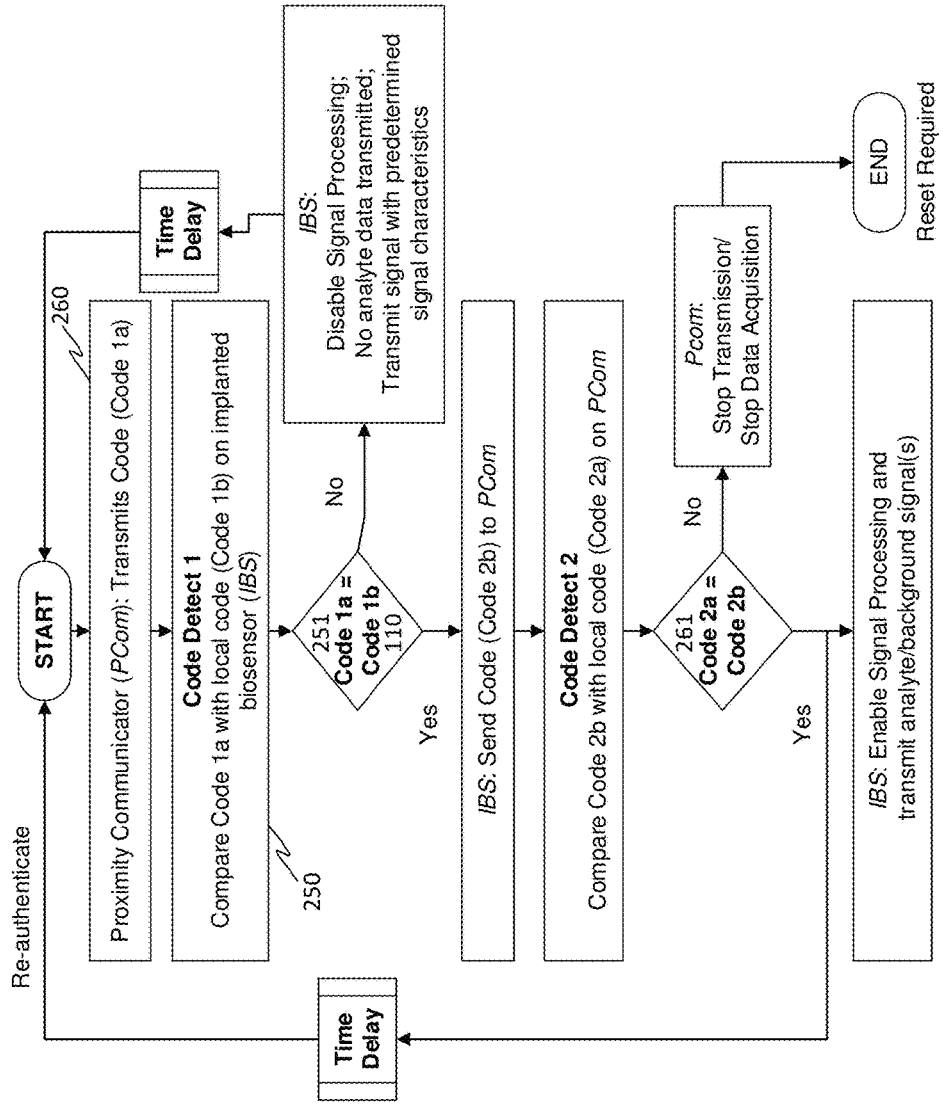
FIG. 2B is a flow diagram illustrating the code detect architecture with a two codes that are associated with the proximity communicator and implantable biosensor, in accordance to one embodiment of the invention.

A second embodiment of the authentication process is shown in FIG. 2B. This embodiment is similar to that from FIG. 2A, except that there are three code detection stages. The third stage of the authentication starts once the proximity communicator 11 receives the second authentication code 251 from the implanted biosensor 12. When the second stage codes do not match, the proximity communicator stops transmission and the device requires a reset. When the codes match, the proximity communicator sends a third code 261 to the implanted biosensor 12 and compares this code with a local code 250 on the implanted biosensor. When the codes do not match, the proximity communicator stops transmission and the device requires a reset. When the codes match, the nonvolatile memory (NVM) 35 of the implanted biosensor 12 is enabled and the analyte data 32 and background data 33 are transmitted to the proximity communicator 11.

Figure 2C:
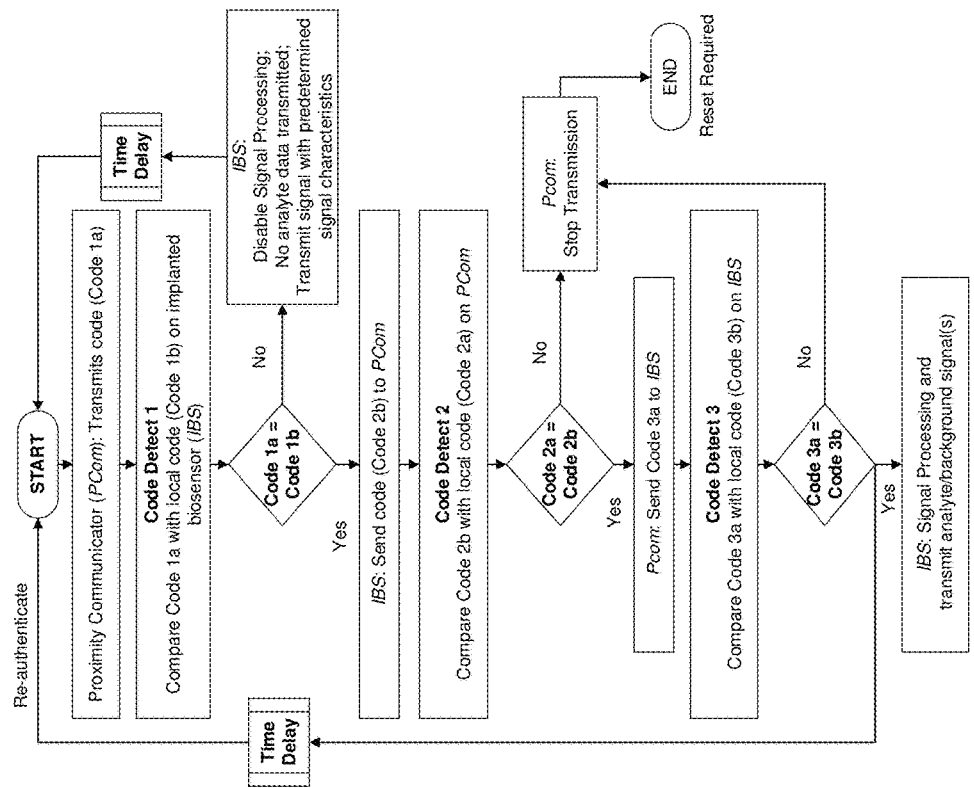
FIG. 2C is a flow diagram illustrating the code detect architecture with a three codes that is associated with the proximity communicator and implantable biosensor, in accordance to one embodiment of the invention.

Referring to FIG. 2C, a third embodiment of the authentication process starts with the implanted biosensor 12 transmitting a code 2500 to the proximity communicator 11. When this transmitted code does not match a local code 1100 on the proximity communicator 11, the proximity communicator stops further transmission and ends the loops (reset required). When the codes match, the proximity communicator 11 sends a second code 2610 to the implanted biosensor 12. The implanted biosensor 12 compares this second code to a local code 2510 on the implanted biosensor. When the codes do not match, the NVM 35 of the implanted biosensor 12 remains disabled and devices attempt to re-authenticate. When the codes match, the NVM 35 of the implanted biosensor is enabled. Re-authentication will be initiated after a preset time delay (e.g. 0-12 hours) and will continue as long as the implanted biosensor is powered.

Figure 2D:
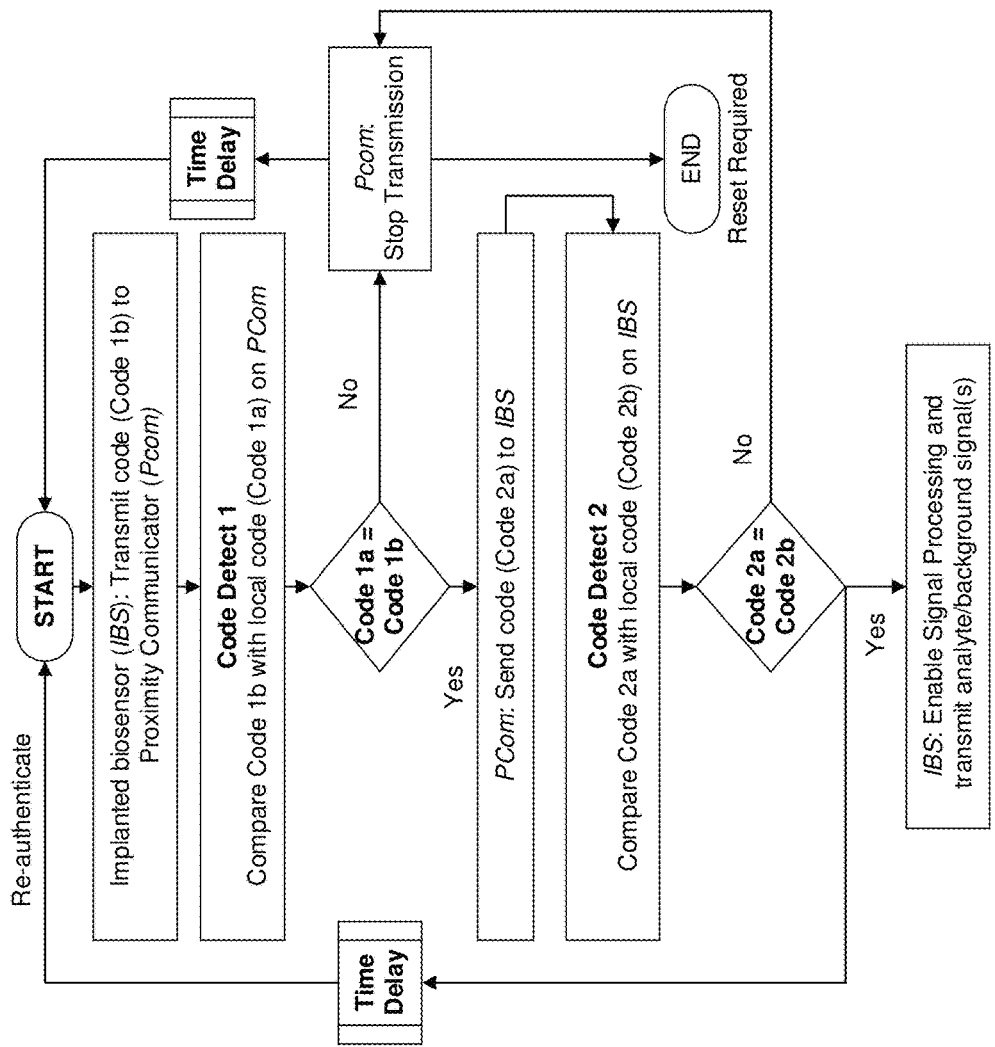
FIG. 2D is a flow diagram illustrating the code detect architecture with a single code initially transmitted by the implantable biosensor, in accordance to one embodiment of the invention.

FIG. 2D illustrates a flow diagram of the code detect architecture with a single code 2500 initially transmitted by the implantable biosensor 12. FIG. 2D follows the same methodology described in FIG. 2B, except that the implanted biosensor initiates communication protocol by transmitting the initiation code to the proximity communicator 11.

Method 2—Metabolite Sensing for General Wellness Use

For the biosensing platform with the authentication architecture described above, a method is to limit or prevent users (i.e. humans, humans acting on behalf of humans or animals, or intelligent computer systems) from using analyte monitoring systems for medical-related decisions. By those skilled in the art (e.g. medical doctors and medical researchers), healthy analyte levels have been determined for many different metabolites FIG. 3. The overall method is to sense, transmit and/or display to the user sufficient information for the user to understand one's general wellness, while averting the user from using such a device to manage and/or diagnose a disease (e.g. diabetes).

Figure 4:
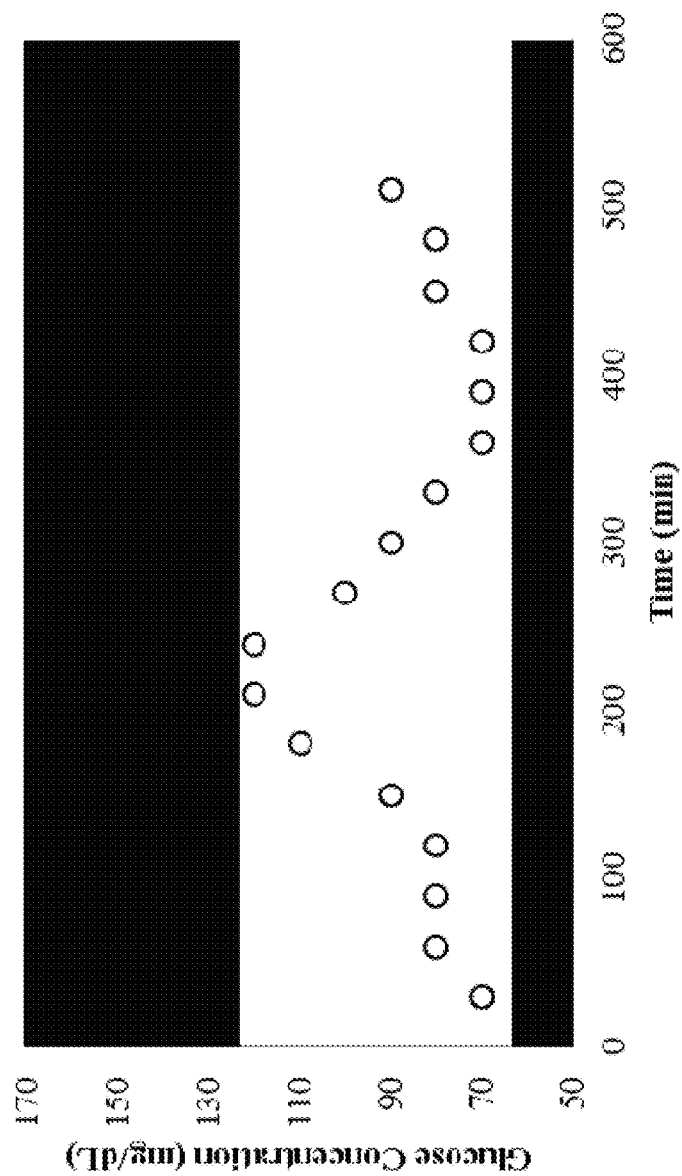
FIG. 4 is a schematic illustrating an example of normal glucose concentrations (mg/dL) vs. time (min).

Method 2a—Adding Limitations to Constant Analyte Monitoring:

Certain limitations can be incorporated into the continuous analyte monitoring platform that will avoid the use of the device for high-risk medical-related decisions. Two limitations are described herein: (1) limit the available range of analyte values FIG. 4 and (2) provide a time delay (e.g. of 1 to 48 hours) to the real-time analyte values. For each of these limitations, the computer system(s) in connection with the biosensing element can include computer algorithms to specifically include each limitation.

Figure 5:
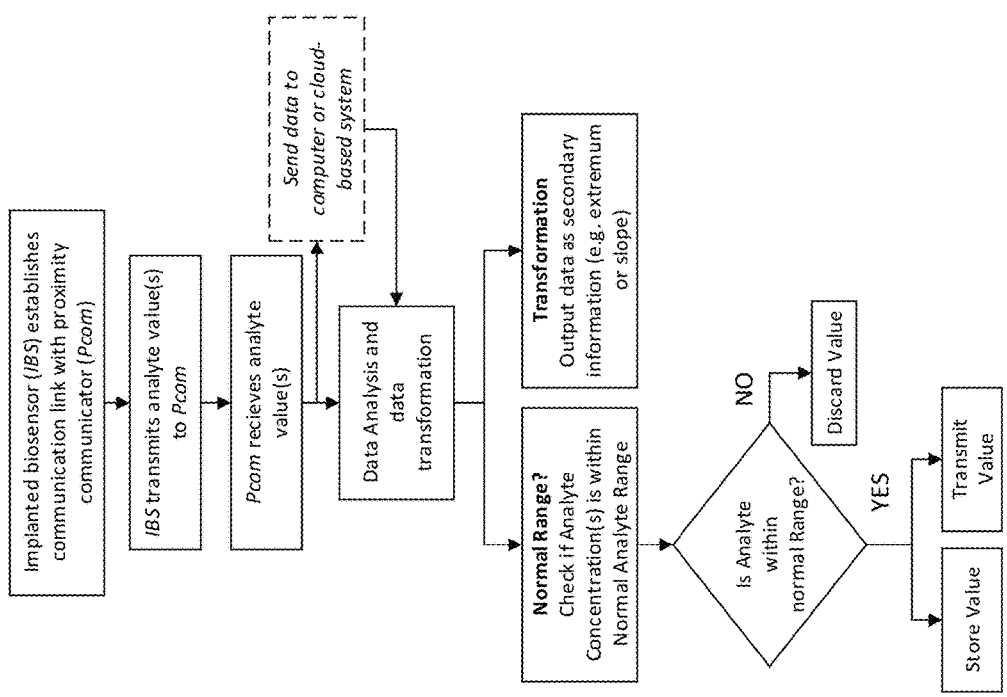
FIG. 5 is a flow diagram illustrating a method that outlines the implementation of analyte sensors for "general wellness use" applications.

Referring to FIG. 5, the available range of the sensor can be designed to only include healthy analyte levels determined by those skilled in the art. As an example, computer algorithms can use signal filtering to exclude levels lower than or equal to the lowest healthy analyte level and exclude levels higher than or equal to the highest healthy analyte level, thus only passing the full range of the healthy metabolite levels. Moreover, the transmission and display of such data can be subject to a time delay. A first example of incorporating a time delay includes adding a time delay to individual data points, i.e. each data point will be delayed for 1 to 48 hours. A second example of incorporating a time delay includes adding a time delay to multiple data points (i.e. a block of data points). To exemplify, all analyte values collected in the previous 1-hour time frame would be grouped into a single bin of data points and then transmitted and displayed to the user at a specific time point (e.g. 30 minutes) from the last recorded timestamp for the block of analyte values.

Method 3—Conversion of Real-time Metabolite Values to Secondary Information:

Another method is for computer algorithm(s) to output secondary information (processed metabolite data) such as metabolic rates (derivatives), as extremum and ranges, and as averages. This information could be used to relate to one's general wellness and, as the user would not have access to the real-time analyte value, medical diagnosis or medical decision making (e.g. calculating an injection dose of insulin) would be mitigated.

Method 3a—Metabolic Rates

Secondary information based on metabolic rates can include: (1) the number of occurrences of high derivatives (metabolite spikes) over a period of time and (2) preprandial and postprandial metabolic rates. The metabolic rates could be displayed as a numeric value (e.g. 10 units/min) or text based (e.g. high or low). In addition, the prepandial and postprandial metabolic rates can be further displayed as a ratio, e.g. to provide a health metric relating analyte absorption and metabolism.

Method 3b—Extremum and Ranges

Extremum values (e.g. maximum and minimum) and ranges can also be calculated and displayed to the user. The extremum values could be established over a specified timeframe. In one example, the timeframe could be a 24-hour period. In a second example, the timeframe could be prior to consuming a meal and extend 2 hours post consuming the meal. Moreover, secondary information on ranges can be provided. An example of a range could be from the preprandial analyte concentration to the maximum postprandial analyte concentration. This range can be used to understand how one's body responds to the consumption of meals and types of food. To promote general wellness, a person can use this information to reduce calorie intake in a short period of time to prevent the occurrence of large spikes in glucose concentrations.

Method 3c—Averaging

Lastly, averages over a specified time can be displayed to the user. The specified timeframe could be a 24-hour period or over a shorter period (e.g. 2 hours). For example, daily averaged values of metabolites could be collected over a period of time such as months to years. This information could be further linked with eating habits and/or fitness activities to promote healthy lifestyle choices.

Method 4—Limiting the Detection Based on Physical Changes at the Electronic-chip Level:

A third method is based on limiting the analyte detection at the electronic-chip level. The electronic-chip level is herein defined as the silicon-based microelectronic chip and the connected biosensing elements (electrodes). Attached to the silicon-based microelectronic chip is a light emitting diode (LED). In one embodiment, electronic circuitry consisting of comparators and combinations of electronics can be implemented to prevent an output signal at both low and high levels of analyte detection. In a second embodiment, the sensitivity of the biosensing elements (electrodes) can be altered based on physical changes, such as the surface area of the electrodes and coatings on the electrodes.

Method 4a—Limit the Detection of a Light-based Biosensing Element

As an example, of which relates to electromagnetic (or light) based detection techniques, the light source can be limited to prevent the detection of low levels of analytes. In this approach, the electromagnetic detector used to detect changes in the light signal can be of low sensitivity to prevent the detection of low levels of the analyte. Moreover, the electromagnetic detector can be designed to become fully-saturated at a certain level (e.g. at 140 mg/dL for glucose concentrations) and thus limit the high levels of the analyte.

Method 4b—Limit the Detection on an Electrode-based Biosensing Element:

This method is based on a system (i.e. a biosensing element) that is designed with a limited range of analyte detection. This method applies to systems that comprise of a biosensing element that consists of electrodes and to biosensing elements that are based on electromagnetic radiation (i.e. light based such as optical or fluorescence). Limiting the range of detection can be achieved by preventing the amount of analyte (e.g. glucose) from reaching the biosensing element. As an example, in order for glucose to reach the working electrode of the biosensing element, glucose must diffuse through multiple layers of a composite coating consisting of glucose-flux limiting polymers such as polyurethane. By precisely controlling the thickness of the polymers and the polymer composition, it is possible to fine tune the rate of glucose and oxygen diffusion. For example, glucose barrier membranes can be used to dictate the lower detectable glucose concentration, while $O_2$ supply (also dictated by the nature and thickness of certain membranes) can dictate the upper glucose concentration detected (by plateauing the electrochemical response of the sensor above 140 mg/dL). Similar lower and upper detection-exclusion schemes can be implemented for other bioanalytes.

An Example of Continuous Glucose Monitoring for General Wellness Use:

Monitoring glucose throughout the day may be used to determine an individual's general wellness by observing how the body processes glucose after meals throughout the day. For healthy individuals, glucose is known to vary between approximately 70 to 140 mg/dL, which depends on factors such as metabolism rate, absorption and the type/amount of food consumed. Postprandial glucose concentrations are higher as the body converts simple and complex carbohydrates into glucose in the gastrointestinal tract. The absorption and metabolism of glucose cause increases and decreases in blood glucose values, respectively. After a meal, especially of foods with a high glycemic index, blood glucose values will increase rapidly and gradually decline as the body metabolizes glucose. Meals that consist mostly of complex carbohydrates (or starches) may cause a slower increase in blood glucose levels as the amount of time to convert the starch into glucose is delayed, resulting in a slower absorption. The rate of change of glucose during or soon after a meal can be related to glucose absorption and whether or not an individual is consuming too much sugar-rich foods during a short period of time. Moreover, the rate of change of glucose starting at a later time point (e.g. one hour later) can relate to an individual's metabolism of glucose. Additional values such as the time to the maximum glucose value after the onset of consuming a meal, glucose concentration amplitude change after each meal, and one's daily glucose range (maximum value–minimum value) can also be used to assess an individual's general wellness. These values, based on healthy individuals with respect to gender, cohort, fitness level, etc. can then be used to establish recommendations to promote general wellness. For example, a rate change of >100 mg/dL/min may indicate poor dietary meal choices or a high calorie meal. Recommendations may be to consume additional foods such as complex carbohydrates, reducing the amount of food during each meal and/or eating more low-calorie meals throughout the day.

As described above, the methods and embodiments described hereinabove and in the several figures may be embodied in the form of computer-implemented processes and apparatuses for practicing those processes. The methods and embodiments described hereinabove and in the several figures may also be embodied in the form of computer program code containing instructions embodied in tangible media, such as floppy diskettes, CD-ROMs, hard drives, or any other computer-readable storage medium, wherein, when the computer program code is loaded into and executed by a computer (or other processing device), the computer (or other processing device) becomes an apparatus for practicing the invention. Existing systems having reprogrammable storage (e.g., flash memory) may be updated to implement the invention. The methods and embodiments described hereinabove and in the several figures may also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments may configure the microprocessor to create specific logic circuits. It should be further appreciated that the methods and embodiments described hereinabove may also be practiced, in whole or in part, via any device suitable to the desired end purpose, such as a computer, iPod, MP3 Player, a PDA, a Pocket PC and/or a Cell phone with connection capability.

It should be appreciated that while the invention has been described with reference to an exemplary embodiment, it will be understood by those skilled in the art that various changes, omissions and/or additions may be made and equivalents may be substituted for elements thereof without departing from the spirit and scope of the invention. Moreover, embodiments and/or elements of embodiments disclosed herein may be combined as desired. In addition, many modifications may be made to adapt a particular situation or material to the teachings of the invention without departing from the scope thereof. Therefore, it is intended that the invention not be limited to the particular embodiment disclosed as the best mode contemplated for carrying out this invention, but that the invention will include all embodiments falling within the scope of the appended claims and/or information. Moreover, unless specifically stated any use of the terms first, second, etc. do not denote any order or importance, but rather the terms first, second, etc. are used to distinguish one element from another.

What is claimed is:

1. A biosensor platform comprising:
    A watch-like, proximity communicator that further comprises of a microprocessor, optical sources, photodetectors, optical circuitry, signal processors, and data communication modules;
    An implantable biosensor, further comprising of sensor(s), sensor interface circuit(s), signal processor(s), electronic multiplexer(s), photovoltaics(s), optoelectronic transmitters and receivers, and nonvolatile memory:
        wherein the photovoltaics are interfaced with a voltage regulator to provide a stable power to the electrical components and circuits in the implantable biosensor,
        wherein the biosensor receives from the optical transmitter located on the proximity communicator coded optical pulses and using at least one photodetector operating at an operable wavelength that converts these optical pulses into electrical pulses,
        wherein the electrical pulses are decoded by a code detect unit,
        wherein the code authentication data is transmitted by the optical transmitter to the photodetector receiver in the proximity communicator,
        wherein the implantable biosensor includes analyte sensors, protein sensors, and physiologic sensors, such that the sensors are connected to electronic circuitry, signal processing unit(s) and multiplexer (s),
        wherein the analyte sensor data is fed to an optical driving circuit a that converts electrical pulses into optical pulses and is transmitted by an optical transmitter to the associated photodetector of the proximity communicator.

2. The implantable biosensor of claim 1, wherein the coded pulses enables the operation of transmitting analyte biosensing data from non-volatile memory to the associated proximity communicator.

3. The implantable biosensor of claim 1, wherein the coded pulses are for biosensor platform to the proximity communication authentication and comprise of a 2 to 256-bit authentication code.

4. The implantable biosensor of claim 1, wherein the coded pulses are for biosensor platform to the proximity communication identification and comprise of a 2 to 256-bit identification code.

5. The implantable biosensor of claim 1, comprising of multiple code detect units.

6. The implantable biosensor of claim 1, comprising of a mode select unit.

7. The proximity communicator of claim 1, comprising of an interface for a smartphone, computer or cloud-based service.

8. The biosensing platform of claim 1, comprising of a computer processing algorithm that stores and/or transmits normal analyte concentrations at or within the normal analyte range, wherein the computer processing algorithm does not store and/or transmit analyte concentrations outside of the normal analyte range, wherein the biosensing platform is intended only for general wellness use.

9. The biosensing platform of claim 1, where its membranes are designed to limit the diffusion of the analyte to reach the sensing platform, and that the maximum analyte concentration is less than the highest value in the normal analyte concentration range.

10. The biosensing platform of claim 1, comprising of an optical, electromagnetic radiation source, wherein the optical source power is regulated to prevent the detection of analyte levels lower than the lowest value in the normal analyte concentration range.

11. The biosensing platform of claim 1, comprising of an optical, electromagnetic radiation source, wherein the source power is regulated to prevent the detection of analyte levels higher than the highest value in the normal analyte concentration range.

12. The biosensing platform of claim 1, comprising of an electromagnetic radiation detector, wherein the detector is regulated to prevent the detection of analyte levels higher than the highest value in the normal analyte concentration range.

13. The biosensing platform of claim 1, comprising of an electromagnetic radiation detector, wherein the detector is regulated to prevent the detection of analyte levels lower than the lowest value in the normal analyte concentration range.

\* \* \* \* \*